United States Patent [19]

Sikkenga

[11] Patent Number: 4,503,282

[45] Date of Patent: Mar. 5, 1985

[54] PROCESS TO CONVERT LINEAR ALKENES SELECTIVELY USING HIGH CONCENTRATIONS OF AMS-1B CRYSTALLINE BOROSILICATE CATALYST

[75] Inventor: David L. Sikkenga, Wheaton, Ill.

[73] Assignee: Standard Oil Company (Indiana), Chicago, Ill.

[21] Appl. No.: 422,742

[22] Filed: Sep. 24, 1982

[51] Int. Cl.$^3$ .............................. C07C 3/20; C07C 5/30
[52] U.S. Cl. ........................................ 585/671; 585/312; 585/322; 585/329; 585/415; 585/525; 585/531; 585/664; 585/670
[58] Field of Search ............... 585/312, 322, 329, 415, 585/417, 418, 419, 510, 520, 525, 531, 664, 666, 670, 671; 252/432

[56] References Cited

U.S. PATENT DOCUMENTS

| | | | |
|---|---|---|---|
| 4,268,420 | 5/1981 | Klotz | 585/641 |
| 4,433,190 | 2/1984 | Sikkenga et al. | 585/660 |
| 4,451,685 | 5/1984 | Nevitt et al. | 585/415 |

Primary Examiner—Delbert E. Gantz
Assistant Examiner—A. Pal
Attorney, Agent, or Firm—Wallace L. Oliver; William T. McClain; William H. Magidson

[57] ABSTRACT

A process to convert a substantially linear alkene, such as n-butene, to isomerized products comprises contacting such alkene under conversion conditions comprising a temperature of above 300° C. to about 650° C. and an alkene reactant partial pressure of less than about 0.4 atmospheres with an AMS-1B borosilicate catalyst composition containing at least 50 wt. % hydrogen from AMS-1B incorporated in an inert binder.

21 Claims, No Drawings

4,503,282

PROCESS TO CONVERT LINEAR ALKENES SELECTIVELY USING HIGH CONCENTRATIONS OF AMS-1B CRYSTALLINE BOROSILICATE CATALYST

BACKGROUND OF THE INVENTION

This invention relates to selective conversion of alkenes and more particularly relates to selective isomerization of normal alkenes, such as normal butenes, using a catalyst composition containing high concentrations of AMS-1B crystalline borosilicate molecular sieve.

In many instances it is desirable to convert an alkene such as normal butene by mechanisms such as structural isomerization and double bond shift. Such converted alkenes then can be reacted further, such as by polymerization or oxidation, to form useful products. Normal alkenes containing four carbon atoms include 1-butene, trans-2-butene and cis-2-butene and are relatively inexpensive feedstocks. Isobutylene is a branched four-carbon alkene useful in the manufacture of polyisobutylenes which can have various properties depending on the manner of polymerization. For example, both crystalline polyisobutylene and viscous polyisobutylene can be manufactured according to well-known processes in the art. In addition, isobutylene is used in the manufacture of methyl-t-butyl ether which is useful as an octane booster in gasoline. Conventionally, butylenes, including isobutylene, are obtained as a by-product from refinery processes such as catalytic or thermal cracking units. For manufacture and uses of butylenes, see Kirk-Othmer, "Encyclopedia of Chemical Technology," Third Edition, Vol. 4, pp. 346-375, incorporated herein by reference.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positiveion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420 and 4,269,813, incorporated by reference herein. According to these patents AMS-1B can be synthesized by crystallizing a source of an oxide of silicon, an oxide of boron, an oxide of sodium and an organic template compound such as a tetra-n-propylammonium salt. The process of this invention uses AMS-1B crystalline borosilicate molecular sieve.

Hydrocarbon conversion processes are known using other zeolitic materials. Examples of such processes are dewaxing of oil stock (U.S. Pat. Nos. 3,852,189, 4,211,635 and Reissue 28,398); conversion of lower olefins (U.S. Pat. Nos. 3,965,205 and 3,960,978 and European Patent Application No. 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocarbons (U.S. Pat. Nos. 3,753,891, 3,767,568, 3,770,614 and 4,032,432); conversion of ethane to aromatics and $C_3^+$ hydrocarbons (U.S. Pat. No. 4,100,218); conversion of straight-chain and slightly branched chain hydrocarbons to olefins (U.S. Pat. Nos. 4,309,275 and 4,309,276); and conversion of $C_4$ paraffins to aromatics (U.S. Pat. No. 4,291,182).

Conversion of $C_4$ hydrocarbons under some conditions is described in commonly assigned U.S. patent application Ser. No. 422,821 in the name of Nevitt, Sikkenga and Jerome, Ser. No. 422,743 in the name of Peters and Klotz, Ser. No. 422,822 in the name of Melquist, and Ser. No. 422,744 in the name of Nevitt and Jerome, all filed of even date herewith and all incorporated by reference herein. The improvement described herein is the discovery that catalyst formulations in which hydrogen form AMS-1B crystalline borosilicate molecular sieve comprises a major portion of the catalyst formulation, and a binder such as alumina comprises a minor portion, show high alkene isomerization activity such that low hydrocarbon partial pressures, high temperatures and short contact times can be used to produce high selectivity to isoalkenes such as isobutylene.

A method to manufacture isobutylene from a normal alkene such as n-butene would be desirable and a method that would isomerize a carbon structure in one step without excessive losses to undesirable by-products would be especially desirable. Further, a process that selectively converts normal butenes to more useful and valuable products such as isobutylene would be advantageous.

SUMMARY OF THE INVENTION

A process to convert a substantially linear alkene, such as n-butene, to isomerized products comprises contacting such alkene under conversion conditions comprising a temperature of above 300° C. to about 650° C. and an alkene reactant partial pressure of less than about 0.4 atmospheres with an AMS-1B borosilicate catalyst composition containing at least 50 wt. % hydrogen form AMS-1B incorporated in an inert binder.

BRIEF DESCRIPTION OF THE INVENTION

In the method of this invention, a substantially linear alkene, such as a normal butene, is converted using a catalyst composition comprising AMS-1B crystalline borosilicate molecular sieve incorporated within an inert inorganic oxide support such that the amount of AMS-1B crystalline borosilicate molecular sieve is at least 50 wt. % of the total catalyst composition. Surprisingly it has been discovered that catalyst compositions using such high fractions of sieve increase selectivity, i.e., decrease by-product formation. The high concentration of sieve in the total catalyst composition produces a catalyst with high isomerization activity such that low hydrocarbon partial pressures, high temperature and short contact times can be used. The result of this discovered process is to convert n-butenes to near equilibrium concentration of isobutylene while minimizing formation of light and heavy by-products.

It has been found that lower alkene reactant partial pressures favor selectivity. Alkene, such as butene, partial pressure in the process of this invention can be lowered by techniques including reducing total system pressure or using an inert diluent such as hydrogen, inert gases or non-reactive hydrocarbons such as methane, ethane, propane or butanes.

For the purposes of this invention a substantially linear alkene includes normal alkenes containing four to about ten carbon atoms and at least one carbon-carbon double bond. The preferable substantially linear alkene useful in this invention is a normal butene. Mixtures of substantially linear alkene can be used in the process of this invention.

The substantially linear alkenes, or mixtures thereof, used in the process of this invention can be in the presence of other substances such as other hydrocarbon-based molecules. Thus, a feedstream used in the process of this invention comprising a substantially linear alkene also can contain other hydrocarbons such as alkanes, methane, aromatics, hydrogen, and inert gases. A process in which partially reacted hydrocarbons are recycled will contain a mixture including alkanes, alkenes, methane and aromatics. Typically a substantially linear alkene feedstream used in this invention contains about 10 to 100 wt. % substantially linear alkene and preferably contains about 50 to 100 wt. % substantially linear alkene.

The catalyst useful in this invention is based on the crystalline borosilicate molecular sieve, AMS-1B, described in U.S. Pat. Nos. 4,268,420, 4,269,813 and 4,285,919, incorporated herein by reference. The useful catalyst for this invention contains AMS-1B in the hydrogen form.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$$0.9 \pm 0.2 M_{2/n}O:B_2O_3:ySiO_2:zH_2O$$

wherein M is at least one cation, n is the valence of the cation, y is between 4 and about 600 and z is between 0 and about 160.

TABLE I

| d-Spacing Å (1) | Assigned Strength (2) |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, sources for cations, an oxide or boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH_-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propyl-ammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0\pm0.2$ using a compatible base or acid such as sodium bisulfate or sodium hydroxide. After sufficient quantities of silicic acid polymer (Ludox) are added with intensive mixing, preferably the pH is again checked and adjusted to a range of about $11.0\pm0.2$. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amino complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VIB and VIII, and ions of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IVB, VB, VIB, VIIB, and VIII, and rare earth elements.

The catalyst useful in this invention is hydrogen-form AMS-1B crystalline borosilicate molecular sieve.

Ion exchange and impregnation techniques are well-known in the art. Typically, an aqueous solution of a cationic species is exchanged one or more times at about 25° to about 100° C. A hydrocarbonsoluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The AMS-1B crystalline borosilicate useful in this invention may be used as an almost pure material in a catalyst or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. Catalytic compositions useful in this invention contain above about 50 wt. % crystalline borosilicate material and preferably contain about 70 wt. % to about 95 wt. % of such material and most preferably contain about 75 wt. % to about 95 wt. % of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a stream of an alkene, such as 1-butene, is contacted with a catalytic material-containing AMS-1B borosilicate-based catalyst. Generally, in the preferable process of this invention a linear alkene is contacted with the above-described AMS-1B borosilicate-based catalyst system in the liquid or vapor phase at a suitable reaction temperature, pressure and space velocity. Generally, suitable reaction conditions include a temperature of above about 300° to about 650° C., a total pressure of about 0.1 to about 100 atmospheres (10 to 10,000 kPa) or higher with hydrogen/hydrocarbon molar ratio of 0 to about 30 or higher at a weight hourly space velocity (WHSV) of about 0.1 to about 40 hr$^{-1}$ and an alkene reactant partial pressure of about 0.01 to about 0.4 atmospheres (1 to 40 kPa). In a typical process scheme, a butene-containing hydrocarbon stream is contacted with such catalyst in a reactor at about 400° to about 600° C. at a total pressure of about 0.2 to about 50 atmospheres (20 to 5000 kPa) with a hydrogen/butene molar ratio of 0 to about 25 at a WHSV of about 0.3 to about 25 hr$^{-1}$ and a butene partial pressure of about 0.02 to about 0.2 atmospheres (2 to 20 kPa). Preferably the butene conversion process of this invention is conducted at about 500° to about 600° C. at a pressure of about 0.3 to about 1.5 atmospheres (30 to 150 kPa) with a hydrogen/butene molar ratio of about 0.5 to about 20 at a WHSV of about 0.5 to about 6 hr$^{-1}$ and a butene partial pressure of about 0.03 to about 0.15 atmospheres (3 to 15 kPa).

The hydrocarbon feed useful in this invention comprises a substantially linear alkene containing four to about eight carbon atoms. Also considered a linear alkene for purposes of this invention is a compound containing a linear alkene segment with four to about ten carbon atoms. It is believed that long chain linear alkenes and compounds containing linear alkene segments or a portion of such alkane or segment may penetrate the molecular sieve structure to contact a catalytic site. Thus, the entire molecule need not be small enough to fit entirely within the cavities of the molecular sieve. The preferable feed contains predominantly n-butenes although typically minor amounts of other $C_4$ hydrocarbon as well as lighter components may be present.

This invention is demonstrated but not limited by the following Examples.

EXAMPLES I-XI

These examples demonstrate a greater selectivity using catalyst compositions containing larger amounts of sieve. AMS-1B crystalline borosilicate molecular sieve in the hydrogen form (containing 0.12 wt. % boron) was prepared according to U.S. Pat. No. 4,268,420 and formed into a catalyst composition either as pure material or containing 25 wt. % gamma alumina in particles sized from 0.0164 to 0.0278 inch diameter. The catalyst particles were placed in a 0.4-inch (inside diameter) fixed bed reactor through which was passed an isobutylene-lean butane-butene feedstock. Product analyses were calculated using n-butane as an internal standard with the assumption that little n-butane was converted at the conditions used. Reaction conditions and analyses are shown in Tables II-VI.

TABLE II

| | | Examples | |
|---|---|---|---|
| | | I | II |
| Conditions | | | |
| Catalyst quantity (grams) | | 1.0 | 1.0 |
| Amount of AMS-1B in Catalyst (wt. %) | | 75 | 75 |
| Reaction Temp. (°C.) | | 499 | 485 |
| Pressure (atmos.) | | 3.0 | 3.0 |
| Hydrogen/hydrocarbon (molar ratio) | | 20.0 | 20.0 |
| Butene partial pressure (atmos.) | | 0.065 | 0.065 |
| WHSV (hr$^{-1}$) | | 9 | 18.5 |
| Product Compositions (wt. %) | Feed | | |
| $C_1$ | 0 | 0.18 | 0.067 |
| $C_2$ | 0 | 0.28 | 0.104 |
| $C_3$ | 0 | 2.87 | 1.52 |
| n-butane | 18.6 | 18.6 | 18.6 |
| isobutane | 35.9 | 36.0 | 35.3 |
| 1-butene | 14.9 | 6.46 | 7.87 |
| isobutylene | 0 | 16.1 | 14.7 |
| trans-2-butene | 17.9 | 8.80 | 10.7 |
| cis-2-butene | 12.7 | 6.12 | 7.65 |
| $C_5$+ | 0 | 4.6 | 3.6 |
| Results | | | |
| Selectivity (%) (isobutylene formed/ n-butene converted) | | 0.67 | 0.76 |
| Approach to Isobutylene Equilibrium (%) | | 93 | 78 |
| n-Butene Conversion (%) | | 53 | 42.4 |

TABLE III

| | | Examples | | |
|---|---|---|---|---|
| | | III | IV | V |
| Conditions | | | | |
| Catalyst quantity (grams) | | 3.0 | 3.0 | 3.0 |
| Amount of AMS-1B in Catalyst (wt. %) | | 100 | 100 | 100 |
| Reaction Temp. (°C.) | | 497 | 498 | 495 |
| Pressure (atmos.) | | 1.0 | 1.0 | 0.10 |
| Hydrogen/hydrocarbon (molar ratio) | | 17.0 | 11.5 | 0 |
| Butene partial pressure (atmos.) | | 0.026 | 0.035 | 0.046 |
| WHSV (hr$^{-1}$) | | 3.7 | 1.9 | 1.9 |
| Product Compositions (wt.%) | Feed | | | |
| $C_1$ | 0 | 0.20 | 0.07 | 0.02 |
| $C_2$ | 0 | 0.23 | 0.22 | 0.20 |
| propane | 1.67 | 1.60 | 1.59 | 1.63 |
| propylene | 1.26 | 2.77 | 3.07 | 3.37 |
| n-butane | 9.86 | 9.86 | 9.86 | 9.86 |
| isobutane | 36.8 | 37.2 | 37.1 | 36.4 |
| 1-butene | 18.5 | 8.34 | 7.30 | 7.13 |
| isobutylene | 1.73 | 19.1 | 20.5 | 20.2 |
| trans-2-butene | 18.5 | 11.8 | 11.1 | 11.1 |
| cis-2-butene | 11.6 | 8.40 | 7.79 | 7.62 |
| $C_5$+ | 0 | 0.51 | 1.4 | 2.38 |
| Results | | | | |
| Selectivity (%) (isobutylene formed/ n-butene converted) | | 87 | 84 | 81 |
| Approach to Isobutylene Equilibrium (%) | | 86 | 95 | 95 |

TABLE III-continued

| | Examples | | |
|---|---|---|---|
| | III | IV | V |
| n-Butene Conversion (%) | 41 | 46 | 47 |

TABLE IV

| | | Examples | | |
|---|---|---|---|---|
| | | VI | VII | VIII |
| Conditions | | | | |
| Catalyst quantity (grams) | | 2.5 | 2.5 | 2.5 |
| Amount of HAMS-1B in Catalyst (wt. %) | | 80 | 80 | 80 |
| Reaction Temp. (°C.) | | 500 | 540 | 570 |
| Pressure (atmos.) | | 0.5 | 0.5 | 0.5 |
| Hydrogen/hydrocarbon (molar ratio) | | 4.9 | 4.9 | 4.9 |
| Butene partial pressure (atmos.) | | 0.038 | 0.038 | 0.038 |
| WHSV (hr$^{-1}$) | | 1.8 | 1.8 | 1.8 |
| Product Compositions (wt. %) | Feed | | | |
| $C_1$ | 0.00 | 0.04 | 0.12 | 0.25 |
| $C_2$ | 0.00 | 0.18 | 0.34 | 0.57 |
| $C_3$ | 2.61 | 3.91 | 3.97 | 4.05 |
| n-butane | 12.1 | 12.2 | 12.0 | 12.0 |
| isobutane | 32.5 | 32.3 | 32.8 | 32.6 |
| 1-butene | 17.4 | 8.74 | 9.16 | 9.45 |
| isobutylene | 2.09 | 16.8 | 17.2 | 17.1 |
| trans-2-butene | 16.5 | 11.1 | 10.8 | 10.4 |
| cis-2-butene | 10.2 | 8.15 | 7.98 | 7.77 |
| $C_5^+$ | 6.57 | 6.44 | 5.67 | 5.84 |
| Results | | | | |
| Selectivity (%) (isobutylene formed/ n-butene converted) | | 91.9 | 93.2 | 91.1 |
| Approach to Isobutylene Equilibrium (%) | | 79.8 | 84 | 87 |
| n-Butene Converted (%) | | 36.4 | 36.7 | 37.3 |

TABLE V

| | | Examples | | |
|---|---|---|---|---|
| | | IX | X | XI |
| Conditions | | | | |
| Catalyst quantity (grams) | | 2.5 | 2.5 | 2.5 |
| Amount of HAMS-1B in Catalyst (wt. %) | | 80 | 80 | 80 |
| Reaction Temp. (°C.) | | 540 | 540 | 540 |
| Pressure (atmos.) | | 1.0 | 0.5 | 0.27 |
| Hydrogen/hydrocarbon (molar ratio) | | 10.8 | 2.0 | 0.5 |
| Butene partial pressure (atmos.) | | 0.040 | 0.075 | 0.085 |
| WHSV (hr$^{-1}$) | | 1.8 | 3.5 | 3.5 |
| Product Compositions (wt. %) | Feed | | | |
| $C_1$ | 0.00 | 1.14 | 0.10 | 0.08 |
| $C_2$ | 0.00 | 1.49 | 0.36 | 0.40 |
| $C_3$ | 2.61 | 5.22 | 4.10 | 4.71 |
| n-butane | 12.1 | 12.4 | 12.0 | 12.0 |
| isobutane | 32.5 | 36.5 | 32.1 | 32.6 |
| 1-butene | 17.4 | 8.49 | 9.05 | 8.78 |
| isobutylene | 2.09 | 14.4 | 16.5 | 16.5 |
| trans-2-butene | 16.5 | 10.1 | 10.6 | 10.2 |
| cis-2-butene | 10.2 | 7.41 | 7.86 | 7.56 |
| $C_5^+$ | 6.57 | 8.78 | 7.27 | 7.17 |
| Results | | | | |
| Selectivity (%) (isobutylene formed/ n-butene converted) | | 68.2 | 86.9 | 82.1 |
| Approach to Isobutylene Equilibrium (%) | | 78 | 82.5 | 85 |
| n-Butene Converted (%) | | 41 | 37.5 | 39.9 |

TABLE VI

| | | Runs | | |
|---|---|---|---|---|
| | | Run A | Ex. XII | Run B |
| Conditions | | | | |
| Catalyst quantity (grams) | | 1.0 | 1.0 | 1.25 |
| Amount of AMS-1B in Catalyst (wt. %) | | 75 | 75 | 20 |
| Reaction Temp. (°C.) | | 284 | 481 | 500 |
| Pressure (atmos.) | | 3.0 | 3.0 | 3.0 |
| Hydrogen/hydrocarbon (molar ratio) | | 19.2 | 7.4 | 18.5 |
| Butene partial pressure (atmos.) | | 0.07 | 0.18 | 0.07 |
| WHSV (hr$^{-1}$) | | 25 | 50 | 16 |
| Product Compositions (wt. %) | Feed | | | |
| $C_1$ | 0 | 0 | 0.4 | 0.056 |
| $C_2$ | 0 | 0 | 0.11 | 0.64 |
| $C_3$ | 0 | 2.25 | 2.16 | 5.37 |
| n-butane | 18.6 | 18.6 | 18.5 | 18.6 |
| isobutane | 35.9 | 35.5 | 36.0 | 35.2 |
| 1-butene | 14.9 | 6.21 | 7.80 | 6.26 |
| isobutylene | 0 | 2.43 | 13.5 | 12.5 |
| trans-2-butene | 17.9 | 15.8 | 10.3 | 8.51 |
| cis-2-butene | 12.7 | 9.98 | 7.63 | 6.27 |
| $C_5^+$ | 0 | 9.3 | 4.0 | 6.5 |
| Results | | | | |
| Selectivity (%) (isobutylene formed/ n-butene converted) | | 18.0 | 69.0 | 49.5 |
| Approach to Isobutylene Equilibrium (%) | | 12 | 75 | 83 |
| n-Butene Converted (%) | | 29.7 | 43.2 | 55.6 |

COMPARATIVE RUN A

After obtaining the results shown in Example II, the temperature was reduced to 284° C. and a conversion reaction was run as described in Example II. Results are presented in Table VI. Although reduced temperatures may be expected to improve selectivity, results from Run A show that selectivity to isobutylene was reduced to only 18%.

EXAMPLE XII

Another conversion reaction was performed using conditions similar to those described in Example II except the hydrogen/hydrocarbon molar ratio was reduced while the total pressure was held constant. The data presented in Table VI show that this resulted in an increase in butene partial pressure and increased by-product formation. Comparisons of data from Examples II and XII indicate that lower butene partial pressures are important for high selectivity to isobutylene.

COMPARATIVE RUN B

A 1.25-gram sample of catalyst containing 20 wt. % hydrogen form AMS-1B crystalline borosilicate (containing 0.55 wt. % boron) molecular sieve was packed in a reactor and tested as described in Example II. The results presented in Table VI illustrate reduced selectivity to isobutylene is obtained with low sieve concentrations in alumina.

EXAMPLES XIII-XX

A catalyst was prepared by supporting hydrogen from AMS-1B on gamma alumina such that there was 80 wt. % sieve in the final calcined catalyst. The catalyst composition was crushed and sieved and 1.88 grams of 0.0164-0.0278 inch particles were packed into a reactor as described in the previous Examples. The reactor was heated to 500° C. in a flow of hydrogen and a butane-butene stream was introduced. The butane-butene feed composition together with product compositions are shown in Table VI.

Examples XIII–XVI illustrate that as butane partial pressure is increased, selectivity to isobutylene decreases due to increased formation of $C_5+$ and light hydrocarbons. Examples XVII–XX illustrate the effect of temperature at lower butene partial pressure. As the temperature decreases, butenes are converted in an increasing amount to $C_5+$ products with lower selectivity to isobutylene.

TABLE VII

| | | | | Examples | | | | | |
|---|---|---|---|---|---|---|---|---|---|
| | | XIII | XIV | XV | XVI | XVII | XVIII | XIX | XX |
| Conditions | | | | | | | | | |
| Catalyst quantity (grams) | | 1.88 | 1.88 | 1.88 | 1.82 | 1.88 | 1.88 | 1.88 | 1.88 |
| Amount of HAMS-1B in Catalyst (wt. %) | | 80 | 80 | 80 | 80 | 80 | 80 | 80 | 80 |
| Reaction Temp. (°C.) | | 500 | 500 | 500 | 500 | 601 | 500 | 400 | 300 |
| Pressure (atmos.) | | 0.25 | 0.5 | 1.0 | 1.5 | 1.0 | 1.0 | 1.0 | 1.0 |
| Hydrogen/hydrocarbon (molar ratio) | | 1.0 | 1.0 | 1.0 | 1.0 | 1.0 | 1.0 | 1.0 | 1.0 |
| Butene partial pressure (atmos.) | | 0.060 | 0.120 | 0.240 | 0.360 | 0.044 | 0.044 | 0.044 | 0.044 |
| WHSV ($hr^{-1}$) | | 1.4 | 2.8 | 5.6 | 8.3 | 0.89 | 1.0 | 1.2 | 1.4 |
| Product Compositions (wt. %) | Feed | | | | | | | | |
| $C_1$ | 0.00 | 0.03 | 0.06 | 0.11 | 0.12 | 1.99 | 0.24 | 0.04 | 0.00 |
| $C_2$ | 0.00 | 0.19 | 0.39 | 0.56 | 0.62 | 3.03 | 0.46 | 0.10 | 0.04 |
| $C_3$ | 2.76 | 5.55 | 6.42 | 8.03 | 8.70 | 7.64 | 4.60 | 6.00 | 8.48 |
| n-butane | 12.2 | 11.5 | 12.4 | 12.6 | 12.6 | 12.2 | 12.5 | 12.3 | 13.0 |
| isobutane | 33.2 | 35.4 | 32.6 | 33.9 | 34.1 | 31.1 | 31.9 | 32.7 | 34.8 |
| 1-butene | 17.5 | 8.70 | 7.36 | 6.61 | 6.25 | 8.14 | 8.06 | 6.68 | 3.83 |
| isobutylene | 2.14 | 15.4 | 16.3 | 14.4 | 13.4 | 14.9 | 17.5 | 14.0 | 8.70 |
| trans-2-butene | 17.0 | 11.0 | 9.63 | 8.78 | 8.33 | 8.92 | 10.7 | 11.3 | 8.83 |
| cis-2-butene | 10.3 | 7.67 | 6.96 | 6.34 | 5.98 | 6.63 | 7.78 | 7.76 | 5.63 |
| $C_5+$ | 4.82 | 4.59 | 8.00 | 8.74 | 9.87 | 5.45 | 6.22 | 9.18 | 16.7 |
| Results | | | | | | | | | |
| Selectivity (%) (isobutylene formed/ n-butene converted) | | 75.5 | 67.4 | 52.8 | 46.2 | 60.2 | 83.8 | 61.8 | 40.9 |
| Approach to Isobutylene Equilibrium (%) | | 78.5 | 88.1 | 86.7 | 85.9 | 91.5 | 86.5 | 69.6 | 57.1 |
| n-Butene Converted (%) | | 39.1 | 46.6 | 51.6 | 54.2 | 47.2 | 40.8 | 42.6 | 59.3 |

What is claimed is:

1. A process to convert a substantially linear alkene to isomerized alkenes with low formation of light and heavy by-products comprising contacting such alkene under conversion conditions comprising a temperature of above 300° C. to about 650° C. and an alkene reactant partial pressure of less than about 0.4 atmospheres with an AMS-1B crystalline borosilicate-based catalyst composition containing at least 50 wt. % hydrogen form AMS-1B incorporated in an inert binder.

2. The process of claim 1 wherein the substantially linear alkene comprises a normal alkene having four to about ten carbon atoms.

3. The process of claim 2 wherein the alkene is a normal butene.

4. The process of claim 1 wherein the catalyst composition contains at least 75 wt. % AMS-1B crystalline borosilicate.

5. The process of claim 3 wherein the normal butene is 1-butene, trans-2-butene, cis-2-butene or a mixture thereof.

6. The process of claim 3 wherein the linear alkene is 1-butene.

7. The process of claim 3 wherein the normal butene comprises from about 10 to 100 wt. % of a feedstream contacting the catalyst.

8. The process of claim 7 wherein the feedstream contains a mixture of normal butene and butanes.

9. The process of claim 4 wherein the substantially linear alkene is normal butene.

10. The process of claim 9 wherein the normal butene comprises 10 to 100 wt. % of a feedstream contacting the catalyst.

11. The process of claim 10 wherein the feedstream contains a mixture of normal butenes and butanes.

12. The process of claims 9, 10 or 11 wherein the butene is 1-butene, trans-2-butene, cis-2-butene or a mixture thereof.

13. The process of claims 9, 10 or 11 wherein the butene is 1-butene.

14. The process of claim 1 wherein the AMS-1B crystalline borosilicate composition is incorporated within an alumina or silica-alumina matrix.

15. The process of claim 13 wherein the AMS-1B crystalline borosilicate content in the matrix ranges from about 75 to about 95 wt. %.

16. The process of claim 14 wherein the AMS-1B crystalline borosilicate content in the matrix ranges from about 75 to about 95 wt. %.

17. The process of claim 1 wherein the conversion conditions are a temperature of about 300° to about 650° C., a total pressure of about 0.1 to about 100 atmospheres, a hydrogen/hydrocarbon molar ratio of 0 to about 30, a weight hourly space velocity of about 0.1 to about 40 $hr^{-1}$ and a alkene reactant partial pressure of about 0.01 to 0.4 atmospheres.

18. The process of claim 17 wherein normal butenes are converted at about 400° to about 600° C. at a total pressure of about 0.2 to about 50 atmospheres with a hydrogen/butene molar ratio of 0 to about 25 at a weight hourly space velocity of about 0.3 to about 25 hr$^{-1}$ and a butene partial pressure of about 0.02 to about 0.2 atmospheres.

19. The process of claim 18 wherein n-butene is converted at about 500° to about 600° C. at a total pressure of about 0.3 to about 1.5 atmospheres with a hydrogen/butene molar ratio of about 0.5 to about 20 and a weight hourly space velocity of about 0.5 to about 6 hr$^{-1}$ and a butene partial pressure of about 0.03 to about 0.15 atmospheres.

20. The process of claim 17, 18 or 19 wherein normal butenes comprise about 10 to 100 wt. % of a feedstream contacting the catalyst.

21. The process of claim 17, 18 or 19 wherein normal butenes comprise about 50 to 100 wt. % of a feedstream contacting the catalyst.

* * * * *